United States Patent [19]
Van Leuven

[11] 4,289,758
[45] * Sep. 15, 1981

[54] LIQUID BIOCIDAL COMPOSITIONS COMPRIING A MIXTURE OF SILVER IONS AND SODIUM PECTATE

[75] Inventor: James W. Van Leuven, Duarte, Calif.

[73] Assignee: Aquatain Partnership, Arcadia, Calif.

[*] Notice: The portion of the term of this patent subsequent to Jan. 22, 1997, has been disclaimed.

[21] Appl. No.: 178,755

[22] Filed: Aug. 18, 1980

Related U.S. Application Data

[60] Continuation of Ser. No. 75,979, Sep. 17, 1979, which is a division of Ser. No. 776,776, Mar. 11, 1977, Pat. No. 4,184,974, which is a continuation-in-part of Ser. No. 693,622, Jun. 7, 1976, abandoned, which is a continuation of Ser. No. 470,629, May 16, 1974, abandoned.

[51] Int. Cl.$^3$ .................. A01N 59/16; C11D 3/48
[52] U.S. Cl. ................... 424/132; 252/106; 424/75; 424/290; 424/361
[58] Field of Search ............... 252/106; 424/75, 132, 424/290, 361

[56] References Cited
U.S. PATENT DOCUMENTS

| | | | |
|---|---|---|---|
| 1,764,417 | 6/1930 | Satow | 424/132 |
| 2,155,361 | 4/1939 | Myers | 536/2 X |
| 2,259,767 | 10/1941 | Myers | 536/2 X |
| 2,373,729 | 4/1945 | Willaman | 536/2 X |
| 3,092,552 | 6/1963 | Romans | 424/132 |
| 3,306,819 | 2/1967 | Farthouat et al. | 536/2 X |
| 3,476,489 | 11/1969 | Mees et al. | 424/164 |
| 3,625,904 | 12/1971 | Nosler at al. | 252/107 |
| 3,634,265 | 1/1972 | Merritt | 252/107 |
| 3,639,575 | 2/1972 | Schmolka | 424/78 |
| 3,785,985 | 1/1974 | Grand | 252/106 |

OTHER PUBLICATIONS

Lesser, "Shampoos"—(Part II), *Soap and Sanitary Chemicals,* Jan. 1951, pp. 38–39.
Schimmel Briefs, "Protein-based Detergents in Shampoos", No. 358, Jan. 1965, Schimmel & Co., Newburgh, N.Y.

*Primary Examiner*—P. E. Willis, Jr.
*Attorney, Agent, or Firm*—Christie, Parker & Hale

[57] ABSTRACT

A liquid biocidal agent that has bacteriostatic and viricidal activities is described. The composition includes about 100 to 400 parts per million sodium polypectate, about 13 to 250 parts per million silver ion, about 4 to 8% glycerine, sufficient base such as ammonium hydroxide to maintain a pH in the range of from about 7.2 to 7.8, and distilled water. The composition is useful for treating Herpes virus, condyloma, and for preventing *Staphylococcus aures* infection.

5 Claims, No Drawings

LIQUID BIOCIDAL COMPOSITIONS COMPRIING A MIXTURE OF SILVER IONS AND SODIUM PECTATE

CROSS-REFERENCES TO RELATED APPLICATIONS

This is a continuation of U.S. patent application Ser. No. 075,979 filed Sept. 17, 1979, which is a division of U.S. patent application Ser. No. 776,776, filed Mar. 11, 1977, now U.S. Pat. No. 4,184,974, which is a continuation-in-part of U.S. patent application Ser. No. 693,622, filed June 7, 1976, now abandoned, which is a continuation of U.S. patent application Ser. No. 470,629, filed May 16, 1974, and now abandoned. The subject matter of the prior applications are incorporated herein by reference.

FIELD OF INVENTION

This invention relates to a liquid biocidal agent containing silver ion and sodium polypectate.

BACKGROUND OF THE INVENTION

Restrictions have been applied to the use of hexachlorophene in skin cleansers due to possible physiological effects. Hexachlorophene has been widely used because of its germicidal or bacteriostatic activity. Iodine containing materials have been used as a topical bacteriostatic agent but many people have very severe reactions to iodine and cannot use such materials. Because of the restrictions it is desirable to substitute a material that is free of substantial germicidal or bacteriostatic action. Such material should be suitable for repetitive use, such as by a surgeon in preparing for surgery.

A difficult infection to combat is caused by Herpes virus in the vagina of some women. This infection is persistent and quite resistant to ordinary medication. There is even some hint in research work that Herpes virus is associated with cervical cancer. It is highly desirable to provide a material that is safe, reliable and arrests Herpes virus infections by topical application.

Sometimes during delivery of infants it is desirable to apply a lubricant to permit manual examination during labor and assist during delivery. Such a lubricant should be harmless to both mother and child and preferably is quite soluble in water so that it can be washed away without hazard from other solvents. It is highly desirable that such a lubricant also have a bacteriostatic effect so that the possibility of infections is minimized.

In considering the compositions provided in practice of this invention, I believe that the most pertinent prior art composition may be a previously marketed hard water hair shampoo comprising about 20% triethanolamine salt of linear dodecyl benzenesulfonic acid, about 30% of lauryl diethanolamide, 7% propylene glycol, 0.15% sodium polypectate, ½% each of ammonium hydroxide and citric acid and about 32 milligrams per liter of silver nitrate, all dissolved or suspended in distilled water. The dominant material in this composition is the sodium polypectate which chelates minerals in hard water and gives an excellent shampoo similar to that obtained with the use of soft water. Propylene glycol and silver salt in the composition in combination retarded spoiling of the polypectate. It has been shown that neither silver nitrate nor propylene glycol acting alone prevents spoilage.

Silver nitrate, silver oxide and related compounds and colloidal dispersions of silver compounds have been used in the past as germicides and for parasiticidal purposes. A colloidal dispersion of 5% silver oxide in mineral oil has been used in mastitis and as an antiseptic ointment in superficial infected lesions of the mucous membrane. Silver nitrate solutions have similarly been used. The use of such silver compounds is accompanied by undesirable side effects.

SUMMARY OF THE INVENTION

There is, therefore, provided in practice of this invention a liquid biocidal composition comprising glycerine in the range from about 4 to 8% by weight, sodium polypectate in the range from about 100 to 400 parts per million, from about 13 to 250 parts per million silver ion, and sufficient water soluble base to maintain a pH in the range of from about 7.2 to 7.8. The balance of the composition is primarily sterile distilled water substantially free of alkaline earth cations, halide ions, and strong acid ions. The silver ion can be added to the composition as silver nitrate.

DESCRIPTION

This invention overcomes the undesirable effects of silver compounds by forming a silver polypectate that is completely stable at the specified concentrations. Silver polypectate in higher concentrations is reduced to metallic silver which is mildly germicidal and viricidal. Surprisingly, when this composition is diluted ionic silver is formed and becomes highly germicidal and viricidal to many organisms. Among the organisms killed are *Staphylococcus aures, Pseudomonas aeroginosa, Escherichia coli,* and *Salmonella choleraesus.* Viricidal activity is obtained against bacteriophage 029, a small DNA virus; bacteriophage 082, a large DNA virus; and Herpes virus.

In addition to the silver ion which is preferably added as silver nitrate in this composition, there is sodium polypectate which has a strong chelating activity with the silver. This is a material obtained from the dilute extract of the inner rind of citrus fruit and is an extremely sensitive composition. A 2% solution of sodium polypectate in water is so viscous that it is nearly a gel at ordinary temperatures. Solutions with a concentration between 0.04% and 1% sodium polypectate display chelating action with many compounds both organic and inorganic, particularly those containing calcium and magnesium. This attribute has been capitalized on by using sodium polypectate as an additive to shampoo to remove hardened calcium and magnesium residues left from previous shampoos. Shampoos containing sodium polypectate are subject to bacterial decomposition, consequently they require the addition of preservatives such as propylene glycol and silver nitrate.

In such a shampoo the dominant compound is sodium polypectate wherein the ratio is one part of the polypectate to 0.003 parts of silver. Tests have been made of such a shampoo against *Staphylococcus aureus* with an initial concentration of $10^5$ organisms per milliliter. After 30 seconds exposure from 61 to 75% of the bacteria are killed. This degree of bacteria kill is unacceptable for a compound to be used as a presurgery scrub or in any situation in which control of Staphylococcus infection is desired.

In the present invention silver is the predominant ingredient since there is about one part of sodium polypectate to every one part of silver. Thus, the concentration of silver relative to sodium polypectate is over 300 times as high as any previous composition. Surprisingly it is found that the bacteria kill with the same total silver concentration, or even less, such as one part sodium polypectate to over 0.03 parts of silver, is between 98.8 and 99.8% in a test similar to that described above using Staphylococcus aureus as the test organism in an initial concentration of 10 per milliliter. Stated another way; with a given silver concentration the effectiveness as a bacteriocide can be increased 100-fold (2 log reduction) by reducing the concentration of sodium polypectate.

The strong action against Staphylococcus aureus makes the composition particularly suitable as a pre-surgery scrub or in other situations where Staphylococcus aureus infection may be a problem. Other materials in the composition, as described in greater detail hereinafter, make it a good lubricant and it is highly advantageous as a sterile lubricant for manual examination during labor and for assistance during delivery. Further, it has been found that when such a composition is used as a vaginal douche the topical application results in suppression of Herpes virus infections. This viricidal activity is highly desirable since such infections are quite resistant to other treatment and are persistent once established. Also, the composition is useful for cleansing human corpses to preserve the corpse prior to burial, treating infections with Herpes virus, and for treating condyloma.

The concentration of silver ion in the composition is in the range of from about 13 to about 250 parts per million. If the silver ion concentration is appreciably below about 13 parts per million by weight the biocidal activity of the composition appears to be reduced. If the concentration is higher than about 250 parts per million by weight, there is some suggestion that the biocidal activity may also be reduced and there is some hazard of undesirable skin coloring. The silver ion is preferably introduced in the composition by way of a silver nitrate solution.

The composition preferably contains at least about 35 parts per million (ppm) silver ion when the composition is to be used against bacteria such as Staphylococcus aureus because 35 ppm is the minimum concentration required to obtain a 99.999% kill in 30 seconds of microbes present on the human hand in a concentration of from about $1.4 \times 10^6$ to $4.6 \times 10^6$. Silver ion concentrations as low as 13 parts per million exhibit viricidal action.

The preferred maximum concentration of silver ion is about 250 ppm because silver is expensive and the addition of more silver beyond 250 ppm to the composition results in little, if any, improvement in performance.

The proportion of sodium polypectate in the composition is in the range of from about 100 to about 400 parts per million by weight. This range of sodium polypectate concentration in combination with other ingredients in the composition provides a viscosity suitable for a variety of purposes including a vaginal douche, a lubricant for manual examination during labor and as an assist during delivery, and as a skin cleanser for use in presurgery scrubbing. The lower concentration of 100 parts per million by weight of sodium polypectate is found sufficient to provide adequate chelating activity with the silver ion to maintain it as a stable composition and inhibit its oxidation or decomposition upon exposure to light. It also appears to inhibit any skin darkening effects. It is believed the sodium polypectate serves to ionize the silver in the composition to yield silver ion, which has biocidal activity. To achieve this ionization effect, the polypectate is in the order of about 0.7-1.4 times the silver ion concentration, and more preferably there is at least about one part sodium polypectate per part silver ion in the composition.

When the concentration of sodium polypectate exceeds about 250 parts per million there seems to be some protective effect on both bacteria and virus so that the biocidal activity of the composition is reduced as much as by a factor of 1000. This is believed due to the polypectate reducing silver ion to metallic silver and thereby interfering with the biocidal action of silver ion.

Furthermore, at higher concentrations of sodium polypectate, the polypectate tends to precipitate on the tissue being treated, thereby leaving a residue on the tissue. However, higher concentrations of sodium polypectate result in improved cleansing action of the compositions. Therefore, preferably a composition according to this invention to be used for cleansing and preserving external tissue of a corpse contains at least about 200 parts per million sodium polypectate because a residue on the skin is not a serious problem with a corpse. Similarly, preferably a composition according to the invention to be used for treating herpes virus and condyloma, for preventing Staphylococcus aureus infection, and as a lubricant at time of birth contains less about 250 parts per million sodium polypectate to avoid leaving residue on the skin.

Sodium polypectate may be obtained commercially or can be prepared by treating pectin with sodium carbonate in order to solubilize it. The polypectate chelates readily with the alkaline earth ions such as calcium and magnesium. This effect helps make the composition readily washable from the surfaces on which it is applied although there is some suggestion that there is a temporary attachment to the skin during scrubbing which enhances exposure to silver ion.

The composition contains from about 3.6 to about 8.5% by weight of water soluble detergent which is non-deleteriously reactive with sodium polypectate. By "non-deleteriously reactive" there is meant a detergent which does not interfere with the chelating activity of sodium polypectate. Examplary of such a detergent is a linear alkyl sulphonate having from about 10 to about 12 carbon atoms in the alkyl chain. Such a sulphonate can be provided in the biocidal composition of this invention by using dodecyl benzene sulfonic acid or water soluble salt thereof in the range of from about 2.5 to about 6% by weight of the composition and triethanolamine in the range of from about 1.1% to about 3% by weight of the composition. Preferably the sulfonic acid and the triethanolamine are reacted stoichiometrically because each of these compounds by itself can irritate human skin.

Commercially available dodecyl benzene sulfonic acid or its water soluble salt can have minor variations in chain length and a few isomers of the dodecyl chain may also be present. Such material is widely used as surface active agents common in many detergent compositions. Such a material is preferred in this composition since it gives good cleaning action, lubricity and appropriate viscosity to the composition without adverse effects.

The viscosity of the final composition is affected by the sulfonic acid or its salt. If the concentration is about 2.5% there appears to be some protective effect and the biocidal activity of the composition may be reduced. If the concentration of the sulfonic acid or its salt is more than about 6% there may be insufficient cleaning action if the composition is used as a presurgery scrub and insufficient lubricity for use as a vaginal douche or delivery lubricant. This range of composition in combination with the other ingredients also assures proper viscosity.

Commercially available triethanolamine can contain mono- and diethanolamine. This material has a cleaning action, but if it is present in concentrations of less than about 1.1%, the cleaning activity of the composition may be decreased. The triethanolamine also affects the viscosity of the composition and is preferably maintained in the stated range to provide utility of the composition for the aforementioned purposes.

For higher viscosity and cleansing action detergent materials such as sodium lauryl sulfate can be used, either alone or in combination with the dodecyl benzene sulfonic acid/triethanolamine. Such materials are suitable in compositions used for scrubbing and can find application in cleansing bodies in mortuaries.

The composition also includes lauryl diethanolamide in the range of from about 2.7 to 6.5% by weight. The commercially available material may include a small fraction of isomers and some minor variations in the length of the carbon chain since the starting material is usually a purified fraction of coconut oil. This material has a substantial cleaning action and if it is present in less than about 2.7% the cleaning activity of the composition may be decreased. The lauryl diethanolamide also has an effect on the viscosity of the composition and it is preferably maintained in the stated range to provide wide utility of the composition for the aforementioned purposes. Although it is by no means certain there may also be a protective effect on various microorganisms when the concentration of diethanolamide is unduly increased and it is preferred to keep the concentration below about 6.5%.

The composition also includes propylene glycol in the range of from about 1.2 to 2.5%. This material also has some bacteriocidal activity which cooperates with that of the silver to enhance the biocidal activity of the composition. It is, therefore, preferred to maintain at least about 1.2% of propylene glycol in the composition. The quantity of propylene glycol can be increased, however, no substantial benefit of increase above about 2.5% has been observed and it is preferred to avoid higher proportions to minimize the cost of the composition.

The composition also includes glycerine in the range of from about 4 to 8%. If there is less than about 4% glycerine in the composition there is a drying action that may leave the skin dried or hardened after repeated usage. If the composition contains more than about 8% glycerine there may be an undue moistening of the skin so that a person's hands feel unduly wet even after rinsing. The glycerine provides optimum skin conditioning action substantially any place on a person's body and in particular provides excellent skin conditioning with repeated and prolonged usage on a person's hands. The glycerine also provides a very soothing action on tender tissue on which the composition may be used. Further, the glycerine is preferably maintained in the range of from about 4 to 8% to maintain a suitable viscosity in the composition for a broad range of utilizations. This also provides an adequate range of lubricity in the composition.

The liquid biocidal composition also includes a small amount of pH adjuster such as a water soluble base to maintain the pH in the range of from about 7.2 to 7.8. This range is important for maintaining the stability of the composition over a prolonged period of time, for effective biocidal action and is also preferred for repeated application of the composition to the skin. At a pH less than 7 the polypectate can gel. A number of buffering compositions of the strong base-weak acid type can be used in the compositions so long as they are compatible with the other materials that are present. The pH adjuster can comprise about 0.03% of the total composition and can be made of ammonium hydroxide. Ammonium hydroxide is found to be quite compatible for use with the combination of sodium polypectate and silver nitrate.

The balance of the composition is primarily sterile distilled water. It is important the composition be substantially free of alkaline earth cations because of the very strong chelating properties of the polypectate. It is also important that the composition be substantially free of halide ions which may react with the silver. It is also important that the compositions be substantially free of strong acid anions such as phosphate, sulphate and the like, since these may be deleterious to long term stability and may adversely affect the pH of the composition if present in substantial quantities.

Typically for greater stability of the composition it may include up to about ½% of perfuming and coloring agents which are otherwise substantially inactive in the composition.

The liquid biocidal composition is compounded quite simply without complex equipment by mixing the ingredients in proper order and proportions at room temperature.

The composition can be used for treating external tissue infected with Herpes virus by applying the composition to the tissue, for preventing infection of external tissue by *Staphylococcus aureus* bacteria by applying the composition to the external tissue, and for preserving or cleansing a human corpse by applying the composition to external tissue of the corpse. It also can be used to aid in delivery of a baby at birth by being applied to vaginal tissue of the baby's mother.

Preferably, the composition is bottled in containers opaque to ultraviolet radiation to prevent the reduction of silver ion to metallic silver. Variations of the composition within the described ranges can be made by varying the proportions of the stated ingredients. Small amounts of alcohols, such as may be used as a solvent for perfume, are acceptable in the composition. Inert stable thickeners such as colloidal silica, hydroxymethylated cellulose and the like can also be used in some compositions to control viscosity. Other suitable additives that will not alter the basic characteristics of the liquid biocidal composition will be apparent to one skilled in the art.

EXAMPLE 1

This example shows the preparation of a 100 gallon batch of a topical cleansing agent according to this invention.

A solution "A" comprising a silver ammonium complex was prepared by combining 123.15 grams of reagent grade silver nitrate (78.2 grams silver), 6,700 grams of fresh distilled water, and 3,300 grams of 28% concentration aqueous ammonia (26° Baume). The components of solution "A" were mixed together by shaking for five minutes in a closed container which was lined with silver and contained no metal stirrer. During the preparation of the topical cleansing agent it is important that the solution "A" does not come into contact with reactant metal or else deactivation of the topical cleansing agent can result.

A solution "B" was prepared by mixing in a homogenizer for five minutes 500 grams glycerine, 78.2 grams sodium polypectate, and 18,000 grams fresh distilled water.

A solution "C" was prepared by dissolving 25 grams FDA #1 and #5 "Kelly Green" in 5.975 kilograms of fresh distilled water.

The topical cleansing agent was then prepared in a silver lined reactor having as a stirrer a silver coated rod with neoprene paddles. To the reactor were added 65 gallons of freshly distilled water, and then sufficient aqueous ammonia to bring the water to a pH of at least 7.2. Then 20 gallons of Carsofoam I-52 were mixed into the contents of the reactor and stirred for five minutes. Carsofoam I-52 is available from Quad Chemical Company of Long Beach, Calif. and contains 9.5% triethanolamine 21.9% dodecylbenzene sulfonic acid, 10.1% propylene glycol, 23.1% lauryl diethanolamide, and 36.2% soft water.

The topical cleansing agent was then packaged in black plastic bottles to avoid degradation of the silver due to sunlight.

EXAMPLE 2

A topical cleansing agent (TCA) identical to the cleansing agent of Example 1 was prepared except that it contained half as much silver and half as much sodium polypectate, i.e., 100 parts per million by weight silver rather than 200 parts per million by weight silver and 100 parts per million by weight sodium polypectate rather than 200 parts per million.

EXAMPLE 3

This example demonstrates the effectiveness of the TCA of Examples 1 and 2 in reducing the bacteria count on the human hand. It also shows that the TCA of Example 1 is more effective than the TCA of Example 2 in reducing bacteria count.

A total of 6 healthy adult subjects, male and female, of mixed age and race were used. All subjects were free of clinical manifestations of dermatoses and none were taking any topical or systemic antimicrobials or oral contraceptives.

For two weeks prior to, and throughout the test period, all subjects avoided the use of medicated soaps, lotions, shampoos, deodorants and similar products. They avoided skin contacts with solvents, detergents and similar materials. All subjects were supplied with Camay soap and rubber gloves for use at home.

Following the two week pretest period, all candidates were screened to determine their baseline counts. Following a 30 second wash with 5 ml bland liquid soap (Baby-San, Huntington Laboratories, Huntington, Ind. 46750) and tap water at 35°–40° C., ad libitum, sterile, prewet surgical gloves were placed on both hands. The standard glove fluid sampling procedure as outlined below was then used to sample both hands. Only subjects whose left and right hand counts were comparable and in the range of 1.5 to $4.0 \times 10^6$ organisms per hand were selected for further testing.

On the test day all subjects scrubbed once and were then sampled (Baseline Samples "A" and "B"); all test scrubbing was done as follows. Subjects placed a sterile surgical glove on one hand. The hands and the forearm of the ungloved hand were wet with tap water and 5 ml. of TCA of Example 1 was pipetted into the palm. Both hands and the one forearm were then washed with the TCA of Example 1 for $2\frac{1}{2}$ minutes, with small amounts of tap water added as need to promote sudsing. A sterile Anchor nylon scrub brush was used to scrub the nail cuticle area. The hands were rinsed and the wash/scrub repeated with another 5 ml. of TCA of Example 1. The hand and arm were thoroughly rinsed and a sterile surgical glove was placed on the hand. A glove fluid sample was taken of this hand. The same procedure was then repeated with the TCA of Example 2 on the unwashed hand.

The glove fluid sampling technique was as follows: Seventy-five ml. of sterile stripping/suspending fluid (0.1% Triton X-100 in 0.1 M phosphate buffer, pH 7.8) was instilled into the glove and the wrist secured by the subject. A technician then massaged the hand through the glove for one minute. Aliquots were withdrawn, diluted and plated in triplicate. Trypticase soy broth with 1% Tween 80 and 0.3% Azolectin was used for all dilutions and trypticase soy agar with 1% Tween 80 and 0.3% Azolectin was used for all plating. Plates were incubated at 32° C. for 48 hours. Counts were determined and microbial numbers calculated.

The results of the test are shown in Table I. Baseline Hand "A" and Hand "B" show the microbial count for each hand before use of a TCA. The "after" columns show the results after use of the TCA's. These results indicate that both the Example 1 and the Example 2 TCA reduced microbial count on the human hand. The TCA cleansing agent having the higher silver content, the TCA of Example 1, was the more effective of the two cleansing agents.

TABLE I

| | Microbial Count/Hand | | | |
|---|---|---|---|---|
| Subject No. | Baseline Hand "A" | After TCA of Example 1 on Hand "A" | Baseline Hand "B" | After TCA of Example 2 on Hand "B" |
| 1 | $3.90 \times 10^6$ | $8.60 \times 10^3$ | $2.60 \times 10^6$ | $1.42 \times 10^4$ |
| 2 | $2.80 \times 10^6$ | $4.00 \times 10^3$ | $2.04 \times 10^6$ | $1.38 \times 10^4$ |
| 3 | $3.40 \times 10^6$ | $2.00 \times 10^4$ | $1.90 \times 10^6$ | $5.60 \times 10^4$ |
| 4 | $1.75 \times 10^6$ | $9.95 \times 10^3$ | $1.63 \times 10^6$ | $7.40 \times 10^4$ |
| 5 | $3.70 \times 10^6$ | $1.13 \times 10^4$ | $3.65 \times 10^6$ | $1.39 \times 10^4$ |
| 6 | $4.00 \times 10^6$ | $6.80 \times 10^3$ | $3.10 \times 10^6$ | $5.40 \times 10^3$ |

EXAMPLE 4

This example also shows the effectiveness of the TCA of Example 1 as a topical cleansing agent.

A total of 30 healthy adult subjects, male and female, of mixed race and age were utilized. All subjects were free of clincial manifestations of dermatoses and none were taking any topical of systemic anti-bacterials or oral contraceptives.

For two weeks prior to, and throughout test period, all subjects avoided the use of medicated soaps, lotions, shampoos, deodorants and similar products. They avoided skin contacts with solvents, detergents and similar materials. All subjects were supplied with Camay soap and rubber gloves for use at home.

Following the two week pretest period, all candidates were screened to determine their baseline counts. Following a 30 second wash with 5 ml. bland liquid soap (Baby-San, Huntington Laboratories, Huntington, Ind. 46750) and tap water at 35°–40° C., ad libitum, both hands were rinsed with sterile distilled water and sterile, pre-wet examining gloves were placed on both hands. The standard glove fluid sampling procedure as outlined below was then used to sample both hands. Only subjects whose left and right hand counts were comparable and in the range of 1.5 to $4.0 \times 10^6$ organisms per hand were selected for further testing. Baseline counts were performed with these subjects on days 3 and 7 of the baseline week and are presented in Table II. All subjects were assigned subject numbers on a random basis at this time.

During the test week all subjects scrubbed once with the TCA of Example 1 on day 1 and then were sampled. They scrubbed in an identical manner on day 2 and were sampled again. Following that sampling, all subjects scrubbed two more times at two hour intervals. On days 3 and 4 all subjects scrubbed 3 times daily at 2-3 hour intervals, but no samples were taken. On day 5 all samples were taken according to the sampling schedule below in Table III.

TABLE II
GLOVE FLUID BASELINE COUNTS
AVERAGE MICROBIAL COUNTS/HAND ($\times 10^6$)

| Subject No. | Day 1 Right | Day 1 Left | Day 3 Right | Day 3 Left | Day 7 Right | Day 7 Left |
|---|---|---|---|---|---|---|
| 1 | 1.68 | 1.94 | 1.73 | 2.04 | 1.67 | 2.09 |
| 2 | 3.00 | 2.25 | 2.15 | 2.43 | 3.06 | 2.85 |
| 3 | 3.95 | 3.73 | 4.00 | 3.61 | 3.83 | 3.26 |
| 4 | 3.18 | 3.74 | 3.43 | 3.36 | 3.05 | 3.45 |
| 5 | 2.10 | 1.66 | 1.95 | 1.48 | 1.91 | 2.36 |
| 6 | 2.24 | 2.58 | 2.63 | 2.75 | 2.33 | 1.96 |
| 7 | 3.45 | 2.87 | 3.11 | 3.71 | 3.26 | 2.90 |
| 8 | 1.83 | 2.14 | 2.00 | 2.66 | 1.95 | 2.17 |
| 9 | 3.55 | 3.71 | 3.76 | 3.34 | 3.45 | 3.21 |
| 10 | 2.89 | 3.95 | 3.50 | 4.00 | 2.97 | 3.66 |
| 11 | 3.75 | 3.23 | 3.46 | 3.08 | 3.71 | 3.46 |
| 12 | 2.30 | 2.24 | 2.61 | 2.20 | 2.73 | 2.35 |
| 13 | 1.96 | 2.40 | 1.98 | 2.30 | 1.95 | 2.15 |
| 14 | 1.95 | 1.83 | 2.10 | 1.76 | 1.93 | 2.11 |
| 15 | 3.16 | 4.00 | 3.83 | 3.95 | 4.00 | 3.15 |
| 16 | 3.96 | 3.71 | 3.91 | 3.43 | 3.79 | 3.51 |
| 17 | 3.33 | 3.00 | 2.91 | 3.05 | 3.45 | 3.06 |
| 18 | 2.24 | 1.76 | 2.33 | 1.61 | 2.54 | 1.79 |
| 19 | 3.24 | 3.36 | 3.84 | 2.27 | 3.95 | 2.51 |
| 20 | 2.40 | 2.67 | 2.21 | 2.67 | 2.65 | 3.15 |
| 21 | 1.61 | 1.50 | 1.73 | 1.85 | 2.10 | 1.61 |
| 22 | 2.36 | 1.80 | 2.27 | 2.10 | 2.40 | 1.90 |
| 23 | 2.20 | 3.11 | 3.00 | 2.84 | 2.96 | 2.65 |
| 24 | 1.55 | 2.10 | 1.76 | 1.84 | 1.87 | 2.10 |
| 25 | 2.71 | 2.93 | 2.61 | 2.73 | 2.95 | 2.61 |
| 26 | 1.83 | 1.77 | 1.95 | 1.43 | 1.86 | 1.95 |
| 27 | 1.66 | 1.84 | 1.79 | 1.51 | 1.73 | 1.64 |
| 28 | 2.36 | 2.55 | 2.54 | 2.79 | 3.14 | 3.53 |
| 29 | 1.61 | 1.55 | 1.73 | 1.59 | 1.84 | 1.79 |
| 30 | 3.11 | 4.00 | 3.27 | 3.65 | 3.71 | 3.86 |
| Average | 2.57 | 2.66 | 2.67 | 2.60 | 2.76 | 2.63 |

TABLE III
Sampling Schedule
Study Number of hands sampled at indicated time after treatment

| Day | 0 Hr. | 1 Hr. | 2 Hrs. | 3 Hrs. | 4 Hrs. | 5 Hrs. | 6 Hrs. |
|---|---|---|---|---|---|---|---|
| Baseline | | | | | | | |
| 1 | 60 | 0 | 0 | 0 | 0 | 0 | 0 |
| 3 | 60 | 0 | 0 | 0 | 0 | 0 | 0 |
| 7 | 60 | 0 | 0 | 0 | 0 | 0 | 0 |
| Test | | | | | | | |
| 1 | 30 | 5 | 5 | 5 | 5 | 5 | 5 |
| 2 | 30 | 5 | 5 | 5 | 5 | 5 | 5 |
| 5 | 30 | 5 | 5 | 5 | 5 | 5 | 5 |

All test period scrubbing was done in an identical manner. The hands and arms were wet with tap water and 5 ml. of test product was pipetted into the palm of one hand. Both hands were washed for 2½ minutes with small amounts of tap water added as needed to promote sudsing. A sterile Anchor nylon scrub brush was used to scrub the nail-cuticle area. The hands were rinsed and the wash/scrub repeated with another 5 ml. of TCA. The hands and arms were thoroughly rinsed and sterile surgical gloves were placed on both hands. Samples were then taken according to the sampling schedule with subjects assigned to groups on a randomnized basis. In all instances the right hand was the 0 time sample and the left hand the sample at the indicated time.

The standard sampling technique was as follows: Seventy-five ml. of sterile stripping/suspending fluid (0.1% Triton X-100 in 0.1 M phosphate buffer, pH 7.8) was instilled into the right hand glove and the wrist secured by the subject. A technician then massaged the hand through the glove for one minute. Aliquots were withdrawn, diluted and plated in triplicate. Trypticase soy broth with 1% Tween 80 and 0.3% Azolectin was used for all dilutions and trypticase soy agar with 1% Tween 80 and 0.3% Azolectin was used for all plating. Plates were incubated at 32° C. for 48 hours. Counts were determined and microbial numbers calculated.

The results of the test are presented in Tables IV-A, IV-B, and IV-C by test days 1, 2, and 5 respectively. The results indicate the effectiveness of a TCA according to this invention in reducing microbial count.

TABLE IV-A
Results of Glove Fluid Study - Test Day 1

| Subject No. | Sample Group | Average Microbial Count/Hand 0 Time | Average Microbial Count/Hand Indicated Time |
|---|---|---|---|
| 1 | 1 Hour | $3.80 \times 10^3$ | $3.45 \times 10^2$ |
| 2 | | $2.10 \times 10^2$ | $3.50 \times 10^1$ |
| 3 | | $4.40 \times 10^3$ | $5.00 \times 10^3$ |
| 4 | | $7.00 \times 10^3$ | $3.40 \times 10^3$ |
| 5 | | $2.30 \times 10^4$ | $6.30 \times 10^3$ |
| 6 | 2 hours | $6.65 \times 10^3$ | $1.76 \times 10^4$ |
| 7 | | $3.35 \times 10^3$ | $3.35 \times 10^3$ |
| 8 | | $7.10 \times 10^3$ | $2.08 \times 10^4$ |
| 9 | | $2.85 \times 10^4$ | $9.90 \times 10^3$ |
| 10 | | $6.20 \times 10^3$ | $5.00 \times 10^3$ |
| 11 | 3 Hours | $6.50 \times 10^3$ | $2.45 \times 10^3$ |
| 12 | | $1.78 \times 10^3$ | $9.50 \times 10^2$ |
| 13 | | $1.02 \times 10^4$ | $7.15 \times 10^3$ |
| 14 | | $1.56 \times 10^3$ | $3.65 \times 10^3$ |
| 15 | | $6.65 \times 10^3$ | $9.20 \times 10^3$ |
| 16 | 4 Hours | $4.35 \times 10^3$ | $5.85 \times 10^4$ |
| 17 | | $1.56 \times 10^4$ | $7.20 \times 10^4$ |
| 18 | | $2.35 \times 10^2$ | $7.65 \times 10^3$ |
| 19 | | $1.68 \times 10^3$ | $2.80 \times 10^4$ |
| 20 | | $1.31 \times 10^4$ | $1.05 \times 10^4$ |
| 21 | 5 Hours | $1.80 \times 10^4$ | $1.65 \times 10^5$ |
| 22 | | $7.50 \times 10^4$ | $4.90 \times 10^4$ |
| 23 | | $8.10 \times 10^3$ | $2.00 \times 10^4$ |
| 24 | | $3.00 \times 10^4$ | $2.20 \times 10^4$ |
| 25 | | $1.21 \times 10^4$ | $5.10 \times 10^4$ |
| 26 | 6 Hours | $6.40 \times 10^3$ | $6.00 \times 10^3$ |
| 27 | | $3.60 \times 10^4$ | $6.20 \times 10^4$ |
| 28 | | $8.00 \times 10^2$ | $7.60 \times 10^4$ |
| 29 | | $5.20 \times 10^3$ | $1.09 \times 10^4$ |
| 30 | | $3.20 \times 10^3$ | $8.70 \times 10^3$ |

TABLE IV-B
Results of Glove Fluid Study - Test Day 2

| Subject No. | Sample Group | Average Microbial Count/Hand 0 Time | Average Microbial Count/Hand Indicated Time |
|---|---|---|---|
| 1 | 1 Hour | $6.40 \times 10^3$ | $1.09 \times 10^4$ |
| 2 | | $1.00 \times 10^1$ | $3.50 \times 10^1$ |
| 3 | | $4.90 \times 10^3$ | $1.08 \times 10^4$ |
| 4 | | $4.55 \times 10^3$ | $1.13 \times 10^3$ |
| 5 | | $6.90 \times 10^3$ | $6.10 \times 10^3$ |
| 6 | 2 Hours | $2.95 \times 10^3$ | $7.90 \times 10^4$ |
| 7 | | $4.65 \times 10^3$ | $1.29 \times 10^4$ |
| 8 | | $8.25 \times 10^3$ | $8.80 \times 10^3$ |

TABLE IV-B-continued
Results of Glove Fluid Study - Test Day 2

| Subject No. | Sample Group | Average Microbial Count/Hand 0 Time | Indicated Time |
|---|---|---|---|
| 9 | | $3.15 \times 10^4$ | $1.28 \times 10^4$ |
| 10 | | $1.60 \times 10^4$ | $2.30 \times 10^4$ |
| 11 | 3 Hours | $5.35 \times 10^3$ | $2.05 \times 10^2$ |
| 12 | | $2.95 \times 10^2$ | $9.50 \times 10^1$ |
| 13 | | $3.85 \times 10^3$ | $4.30 \times 10^2$ |
| 14 | | $1.38 \times 10^4$ | $2.31 \times 10^4$ |
| 15 | | $9.45 \times 10^2$ | $1.08 \times 10^3$ |
| 16 | 4 Hours | $3.10 \times 10^3$ | $2.25 \times 10^4$ |
| 17 | | $1.36 \times 10^4$ | $1.31 \times 10^4$ |
| 18 | | $3.50 \times 10^2$ | $9.75 \times 10^3$ |
| 19 | | $7.10 \times 10^3$ | $8.95 \times 10^3$ |
| 20 | | $3.80 \times 10^3$ | $4.55 \times 10^3$ |
| 21 | 5 Hours | $4.00 \times 10^3$ | $8.00 \times 10^4$ |
| 22 | | $8.00 \times 10^3$ | $1.06 \times 10^4$ |
| 23 | | $5.00 \times 10^2$ | $3.60 \times 10^4$ |
| 24 | | $4.40 \times 10^3$ | $7.40 \times 10^2$ |
| 25 | | $3.90 \times 10^3$ | $1.16 \times 10^4$ |
| 26 | 6 Hours | $2.80 \times 10^4$ | $1.10 \times 10^4$ |
| 27 | | $1.84 \times 10^4$ | $1.60 \times 10^1$ |
| 28 | | $1.30 \times 10^3$ | $9.10 \times 10^4$ |
| 29 | | $7.80 \times 10^3$ | $2.55 \times 10^4$ |
| 30 | | $1.70 \times 10^3$ | $5.00 \times 10^3$ |

TABLE IV-C
Results of Glove Fluid Study - Test Day 5

| Subject No. | Sample Group | Average Microbial Count/Hand 0 Time | Indicated Time |
|---|---|---|---|
| 1 | 1 Hour | $2.95 \times 10^3$ | $1.52 \times 10^3$ |
| 2 | | $4.00 \times 10^1$ | $2.00 \times 10^1$ |
| 3 | | $9.80 \times 10^3$ | $9.65 \times 10^3$ |
| 4 | | $2.95 \times 10^3$ | $1.40 \times 10^3$ |
| 5 | | $7.65 \times 10^3$ | $6.80 \times 10^4$ |
| 6 | 2 Hours | $6.20 \times 10^3$ | $2.55 \times 10^4$ |
| 7 | | $1.00 \times 10^3$ | $2.50 \times 10^3$ |
| 8 | | $1.00 \times 10^4$ | $5.40 \times 10^3$ |
| 9 | | $1.14 \times 10^4$ | $4.15 \times 10^3$ |
| 10 | | $1.14 \times 10^4$ | $1.54 \times 10^3$ |
| 11 | 3 Hours | $3.90 \times 10^3$ | $8.20 \times 10^2$ |
| 12 | | $2.20 \times 10^3$ | $3.25 \times 10^2$ |
| 13 | | $1.29 \times 10^3$ | $7.10 \times 10^2$ |
| 14 | | $8.25 \times 10^3$ | $2.20 \times 10^4$ |
| 15 | | $3.45 \times 10^3$ | $4.00 \times 10^3$ |
| 16 | 4 Hours | $1.22 \times 10^3$ | $1.41 \times 10^4$ |
| 17 | | $1.31 \times 10^4$ | $1.16 \times 10^4$ |
| 18 | | $8.50 \times 10^1$ | $8.95 \times 10^2$ |
| 19 | | $6.45 \times 10^3$ | $9.50 \times 10^3$ |
| 20 | | $1.36 \times 10^3$ | $2.90 \times 10^3$ |
| 21 | 5 Hours | $4.80 \times 10^3$ | $1.60 \times 10^4$ |
| 22 | | $2.30 \times 10^3$ | $1.82 \times 10^4$ |
| 23 | | $1.10 \times 10^3$ | $8.10 \times 10^3$ |
| 24 | | $5.60 \times 10^3$ | $2.40 \times 10^3$ |
| 25 | | $6.80 \times 10^3$ | $4.50 \times 10^3$ |
| 26 | 6 Hours | $4.50 \times 10^3$ | $1.87 \times 10^4$ |
| 27 | | $1.36 \times 10^4$ | $7.20 \times 10^3$ |
| 28 | | $6.20 \times 10^3$ | $6.70 \times 10^4$ |
| 29 | | $4.50 \times 10^3$ | $5.00 \times 10^3$ |
| 30 | | $6.80 \times 10^2$ | $2.00 \times 10^3$ |

TABLE V-A
Results of Glove Fluid Study - Test Day 1

| Subject No. | Sample Group | Average Microbial Count/Hand 0 Time | Indicated Time |
|---|---|---|---|
| 1 | 1 Hour | $3.80 \times 10^3$ | $3.45 \times 10^2$ |
| 2 | | $2.10 \times 10^2$ | $3.50 \times 10^1$ |
| 3 | | $4.40 \times 10^3$ | $5.00 \times 10^3$ |
| 4 | | $7.00 \times 10^3$ | $3.40 \times 10^3$ |
| 5 | | $2.30 \times 10^4$ | $6.30 \times 10^3$ |
| 6 | 2 Hours | $6.65 \times 10^3$ | $1.76 \times 10^4$ |
| 7 | | $3.35 \times 10^3$ | $3.35 \times 10^3$ |
| 8 | | $7.10 \times 10^3$ | $2.08 \times 10^4$ |
| 9 | | $2.85 \times 10^4$ | $9.90 \times 10^3$ |
| 10 | | $6.20 \times 10^3$ | $5.00 \times 10^3$ |

TABLE V-A-continued
Results of Glove Fluid Study - Test Day 1

| Subject No. | Sample Group | Average Microbial Count/Hand 0 Time | Indicated Time |
|---|---|---|---|
| 11 | 3 Hours | $6.50 \times 10^3$ | $2.45 \times 10^3$ |
| 12 | | $1.78 \times 10^3$ | $9.50 \times 10^2$ |
| 13 | | $1.02 \times 10^4$ | $7.15 \times 10^3$ |
| 14 | | $1.56 \times 10^3$ | $3.65 \times 10^3$ |
| 15 | | $6.65 \times 10^3$ | $9.20 \times 10^3$ |
| 16 | 4 Hours | $4.35 \times 10^3$ | $5.85 \times 10^4$ |
| 17 | | $1.56 \times 10^4$ | $7.20 \times 10^4$ |
| 18 | | $2.35 \times 10^2$ | $7.65 \times 10^3$ |
| 19 | | $1.68 \times 10^3$ | $2.80 \times 10^4$ |
| 20 | | $1.31 \times 10^4$ | $1.05 \times 10^4$ |
| 21 | 5 Hours | $1.80 \times 10^4$ | $1.65 \times 10^5$ |
| 22 | | $7.50 \times 10^4$ | $4.90 \times 10^4$ |
| 23 | | $8.10 \times 10^3$ | $2.00 \times 10^4$ |
| 24 | | $3.00 \times 10^4$ | $2.20 \times 10^4$ |
| 25 | | $1.21 \times 10^4$ | $5.10 \times 10^4$ |
| 26 | 6 Hours | $6.40 \times 10^3$ | $6.00 \times 10^3$ |
| 27 | | $3.60 \times 10^4$ | $6.20 \times 10^4$ |
| 28 | | $8.00 \times 10^2$ | $7.60 \times 10^4$ |
| 29 | | $5.20 \times 10^3$ | $1.09 \times 10^4$ |
| 30 | | $3.20 \times 10^3$ | $8.70 \times 10^3$ |

EXAMPLE 5

This example shows preparation of another composition according to this invention, the composition exhibiting viricidal activity. The composition has a lower silver concentration than the TCA's of Examples 1 and 2. The biocidal composition comprises a linear alkyl sulphonate having from about 10 to 12 carbon atoms in the alkyl chain in the range from about 3 to 4.5% by weight, lauryl diethanolamide in the range of from about 2.5 to 3.8% by weight, propylene glycol in the range from about 1.75% to 2.25% by weight, glycerine in the range from about 4 to 8% by weight, sodium polypectate in the range from about 100 to 400 parts per million, silver ion in the range of from about 13 to 30 parts per million, sufficient strong base-weak acid buffer to maintain a pH in the range from about 7.1 to 7.5, and a balance of primarily sterile distilled water free of alkaline earth cations, halide ions, and strong acid ions. The buffer can comprise about 300 parts per million of about 50% citric acid, 50% ammonium hydroxide. Subsequent to preparing this composition, it was learned that it is preferred not to use citric acid in the buffer since it can cause precipitation of the silver.

More specifically, a stock solution "A" was prepared having 10 grams of silver nitrate per liter. A solution "B" having 50 grams of citric acid per liter was prepared. A solution "C" was made up by mixing 120 grams of sodium polypectate with a liter of glycerine for about 3 minutes and then adding 16 liters of sterile distilled water. To this mixture there were added 920 milliliters of solution "A", and two liters of solution "B".

Solution "C" was then added to 20 gallons of a solution of linear alkyl sulphonate (21%), lauryl diethanolamide (19%), and propylene glycol (10%) to which was added about 1 liter of perfume. After these materials were thoroughly mixed, 7.9 gallons of 95% glycerine were added and then again the mixture was thoroughly mixed. A sufficient quantity of sterile distilled water was added to make a total of 100 gallons of finished product. A colorant can be added after the product has been finished to yield the desired hue or, if preferred, it can be added at an earlier stage.

EXAMPLE 6

This example shows the effectiveness of the composition of Example 5 in treating condylomata acuminata (condyloma).

Thirty-seven cases of condyloma were diagnosed and treated. Twenty-five of the cases were treated with a topical application of a 25% solution of podophyllin in benzoine or a topical application of bichloroacetic acid. Podophyllin or acid was applied once a week for two to three months until all condyloma growth had disappeared.

In twelve cases treatment included use of podophyllin or bichloroacetic acid and in addition application of the composition of Example 5. The composition of Example 5 was used by swabbing the rectal area and rinsing with water. This was done by the patient after each bowel movement, at approximately mid-day and before retiring at night.

Significantly better results were obtained by use of treatment with podophyllin or bichloroacetic acid in combination with washing the affected area with the composition of Example 6 compared to using podophyllin alone or bichloroacetic acid alone. Most importantly, the patients using the composition of Example 6 were cleared of condyloma growths at about one-half the time required for clearing when treated with podophyllin alone or bichloroacetic acid alone.

EXAMPLE 7

This example shows the effectiveness of the composition of Example 5 in treating infection by herpes simplex virus. Ten patients having herpes virus infection in the perineal area were treated with a conventional silver nitrate applicator made by Arzol Chemical Company, the applicator comprising a composition consisting of 75% silver nitrate and 25% potassium nitrate. The lesion was painted and rubbed with the applicator. Following this treatment, the patients applied the composition of Example 1 to their lesion and rinsed with water. The composition was used three or four times per day.

Another ten patients were treated with the composition of Example 1 without the use of the conventional silver nitrate applicator.

In all twenty cases, the lesion was abated within a week, and where treatment was continued with the composition of Example 5, no recurrences were observed. Experience with conventional silver nitrate applicator alone indicates that typically ¼ of the lesions treated with just conventional silver nitrate applicators require a second treatment about a week later, and approximately 5 to 10% of the patients have recurrences in 1 to 6 months. Thus use of the composition of Example 5 either alone or with conventional silver nitrate applicator gives superior results compared to conventional silver nitrate applicator used alone.

EXAMPLE 8

This test was conducted to determine the effect of raising the ratio of sodium polypectate to silver ion on the effectiveness of the biocidal composition of this invention against *Pseudomonas aeurginosa* organisms.

Three compositions were prepared, 8A, 8B, and 8C. The compositions were identical to the topical cleansing agent of example 1 except each composition contained only 35 ppm silver ion, and composition 8A contained 50 ppm sodium polypectate, composition 8B contained 75 ppm sodium polypectate, and composition 8C contained 100 ppm sodium polypectate.

The test used was a modified version of the A.O.A.C. Germicidal Test on Liquid Soap. Initial numbers of innoculating organisms, which were *Pseudomonas aeurginosa*, were determined by innoculating 40 ml of phosphate buffer dilution blanks and then performing a plate count. The original innoculation was 380,000,000 Pseudomonas per milliliter.

Forty milliliters of each composition were innoculated with the test organisms and then plate counts were performed after 30 seconds exposure and after 60 seconds exposure. The dilution bottles contained a neutralizer.

The results are presented in Table 6. The results indicate that increasing the ratio of sodium polypectate to silver ion increased the percentage kill.

TABLE VI

| Composition | Silver Ion (ppm) | Sodium Polypectate (ppm) | Survivors ($\times 10^6$) | | % Kill | |
|---|---|---|---|---|---|---|
| | | | 30 Seconds | 60 seconds | 30 seconds | 60 Second |
| 8A | 35 | 50 | 100 | 68 | 73.7 | 82.1 |
| 8B | 35 | 75 | 84 | 60 | 77.9 | 84.2 |
| 8C | 35 | 100 | 48 | 29 | 87.4 | 92.4 |

Although limited examples of preparation of liquid biocidal composition according to practice of this invention have been described herein, many modifications and variations will be apparent to one skilled in the art. It is therefore to be understood that within the scope of the appended claims the invention may be practiced otherwise than as specifically described.

What is claimed is:

1. A biocidal composition comprising:
   sterile distilled water substantially free of alkaline earth cations, halide ions and strong acid anions containing:
   sodium polypectate in the range of from about 100 to 400 parts per million;
   silver ion in the range of from about 13 to 250 parts per million;
   glycerine in the range of from about 4 to 8% by weight; and
   sufficient water soluble base to maintain a pH in the range of from about 7.2 to 7.8.

2. A composition as recited in claim 1 containing at least about 35 parts per million silver ion.

3. A composition as recited in claim 2 containing up to about 250 parts per million of sodium polypectate.

4. A composition as recited in claim 1 containing up to about 250 parts per million of sodium polypectate.

5. A composition as recited in claim 1 wherein the water soluble base comprises ammonium hydroxide.

* * * * *

UNITED STATES PATENT AND TRADEMARK OFFICE
CERTIFICATE OF CORRECTION

PATENT NO. : 4,289,758

DATED : September 15, 1981

INVENTOR(S) : James W. Van Leuven

It is certified that error appears in the above—identified patent and that said Letters Patent is hereby corrected as shown below:

```
In the TITLE, "COMPRIING" should be -- COMPRISING --.
Column 4, line 26, --than-- should be inserted before "about";
Column 4, line 42, "Examplary" should be --Exemplary--.
Column 6, line 25, "stability" should be --salability--.
Column 7, line 20, a comma should be inserted after
                   "triethanolamine".
Column 8, line 4,  "need" should be --needed--;
Column 8, line 53, "of" should be -- or --.
Column 14, line 65, "bydroxide" should be -- hydroxide --.
```

Signed and Sealed this

First Day of December 1981

[SEAL]

Attest:

Attesting Officer

GERALD J. MOSSINGHOFF

Commissioner of Patents and Trademarks